US00PP07820P

United States Patent [19]

Teeple et al.

[11] Patent Number: Plant 7,820

[45] Date of Patent: Mar. 10, 1992

[54] APPLE CULTIVAR 'TEEPLE RED EMPIRE'

[75] Inventors: Harold F. Teeple; Russell H. Teeple; John B. Teeple, all of Wolcott, N.Y.

[73] Assignee: Cornell Research Foundation, Inc., Ithaca, N.Y.

[21] Appl. No.: 468,411

[22] Filed: Jan. 9, 1990

[51] Int. Cl.[5] ..... A01H 5/00

[52] U.S. Cl. ..... Plt./34

[58] Field of Search ..... Plt./34

[56] References Cited

PUBLICATIONS

Brooks, R. M. et al., "Empire" *Register of New Fruit and Nut Varieties* 1972 Univ. of California Press, Berkeley p. 31.

New York's Food and Life Sciences Bulletin #41, May 1974 pp. 1-15 "Apple rootstock problems and potentials"—Cummins et al.

New York's Food and Life Sciences Bulletin, #134 Fall 1990 "Royal Empire Apple"—Brown et al.

*J. Amer. Soc. Hort. Sci.*, 116; 1991 (in press)—Robinson, F. L., et al.

*Primary Examiner*—James R. Feyrer

*Attorney, Agent, or Firm*—Jones, Tullar & Cooper

[57] ABSTRACT

An apple tree, 'Teeple Red Empire', a sport of 'Empire' which is significantly redder than 'Empire' but otherwise substantially identical to 'Empire'.

7 Drawing Sheets

BACKGROUND OF THE INVENTION

1. Field of the Invention

This invention is a new and distinct apple cultivar 'Teeple Red Empire' is exceptional for the greater amount of red color on the surface of the fruits than on fruits of the original cultivar 'Empire'. In all other respects it is similar to 'Empire'.

The 'Teeple Red Empire' was discovered as a limb sport on a tree of 'Empire' in an orchard behind Russell Teeple's house, RD #3, Wolcott, N.Y. 14590. The branch was first noticed as bearing redder fruits in 1986. It has continued to bear fruits that are distinctly redder than the fruits on the remainder of the tree (FIGS. 1, 2 and 3). The extent of the sported limb was carefully marked (FIG. 4). Buds were taken from the sported branch and budded onto M9 rootstocks. These trees were planted in another orchard in 1988.

2. Description of Related Art

In early October, 1988, Dr. R. L. Andersen, Ken Livermore, and Dr. R. E. Way, Pomologists at the NYS Agricultural Experiment Station at Geneva, were invited to see the fruit of the sport on the tree. They agreed that there was significantly more red on the fruit of the sported limb than there was on the unsported part of the tree or on nearby 'Empire' trees on limbs in similar positions.

'Teeple Red Empire' is a major improvement over the original cultivar because its greater color will permit a higher proportion of the fruit to quality for the extra fancy grade.

No differences have been observed between this new cultivar and the original variety 'Empire', except the amount of red color on the skin. Such things as tree shape and bearing habit, time of leafing and bloom, leaf shape and color, the color and size of the flowers (FIGS. 5 and 6), pollination requirements the time of fruit maturity, or the size and shape of the fruit of 'Teeple Red Empire' are identical to 'Empire'. Only the color is different.

Also, Dr. Martin Goffinet of the Department of Horticultural Science, NYS Agricultural Experiment Station, examined the fruits of the 'Teeple Red Empire' histologically. He found that the very dark red or maroon areas of the sport and the normal 'Empire' had the same distribution of red coloration i.e. almost all of the epidermal cells and those of the outer 2 or 3 hypodermal layers were pigmented. Similarly, in the greenish yellow areas of both the sport and 'Empire' itself, only the occasional cell of the epidermal layers had pink to red vacuolar anthocyanins. The areas of the fruits with pink to light red colored skin had intermediate amount of epidermal and subepidermal cells that were pigmented in both the sport and the original variety. So the difference in color between the two kinds of fruit is a matter of the amount of surface that is colored rather than the quality of the pigmentation.

Evidence of the similarity in the maturity of the red sport and of the normal cultivar is presented in Table 1 where the pressure test reading and the soluble solids readings on 5 apple are compared for 1988 and 1989. The pressure test utilizes the firmness of the fruit as a measure of maturity and soluble solids measures the amount of sugar in the juice as an indication of maturity. The cultivars are quite similar for both years.

TABLE 1

Maturity of 'Teeple Red Empire' and 'Empire' harvested on the same day in 1988 and 1989.

| Variety | Year | Soluble Solids | Pressure Test |
|---|---|---|---|
| Normal 'Empire' | 1988 | 12.5 | 11 |
| 'Teeples Red Empire' | 1988 | 13.0 | 14 |
| Normal 'Empire' | 1989 | 13.0 | 15.4 |
| 'Teeples Red Empire' | 1989 | 13.0 | 15.5 |

Trees of the 'Teeple Red Empire' and the normal cultivar were budded on M9 rootstocks in 1987. These were planted in the orchard in 1988. There were a few fruit set on these trees in 1989, but unfortunately the birds attached and destroyed them before pictures could be taken to document the increase in color.

Cummins et al, 1974, *New York's Food and Life Sciences Bull.*, No. 41 pp. 1-15, shows 'Empire' on M-9 rootstock produces fruit three years from planting.

SUMMARY OF THE INVENTION

'Teeple Red Empire' is a stable new cultivar. While it takes five to six years for an 'Empire' seedling tree to begin to bear, this time period can be greatly reduced by propagation on dwarfing rootstocks. M-9 rootstock induces precocious bearing. The 'Teeple Red Empire' cultivars, which were examined for stability were all 'Teeple Red Empire' budded onto M-9 rootstocks. Several hundred trees of 'Teeple Red Empire' have been propagated at Teeples' Farm in Wolcott, N.Y. No instability has been noted. In 1990, at least sixteen bushels of fruit were harvested, with the fruit being distinguished from 'Empire' in the manner described herein. There is a clear distinction and specificity in color between 'Empire' and 'Teeple Red Empire' which establishes novelty.

DESCRIPTION

The fruit of 'Teeple Red Empire' is distinctly redder than the original 'Empire'. The sport is estimated to have an average of 90% of the surface covered with dark purplish and red stripes hwere as normal Empire would have an estimated 75% of the surface of similar dark purplish red.

Although 'Empire' can have fruit up to 100% colored, this is all too rare an occurrence. It has been demonstrated that even under the most optimum cultural conditions of open-tree training and summer pruning (procedures that maximize fruit color), the color of 'Empire' average 85%. In our experience, 'Teeple Red Empire' showed 95% to 100% of the surfaces fruit colored compared to 60% to 100% of the standard 'Empire'. A visit to any grocery store selling 'Empire' would also show the degree of bi-colored fruit that is evident within standard 'Empire' produced commercially.

Figure 1:
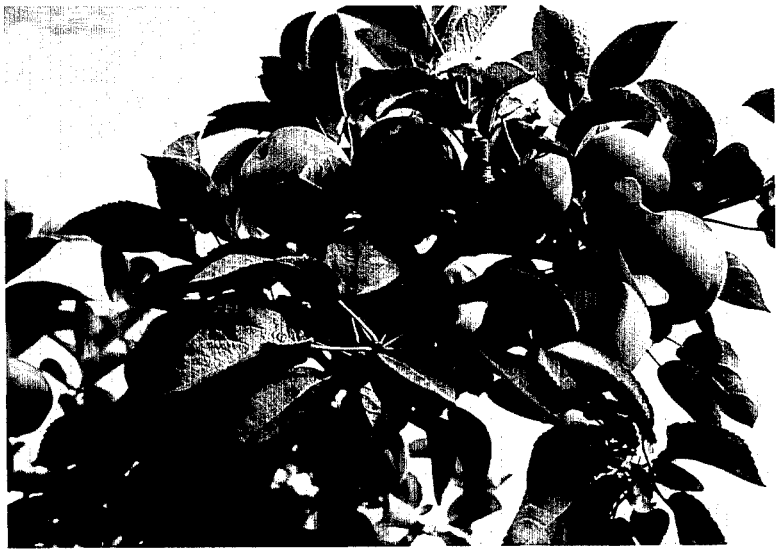
FIG. 1—Fruit of the 'Teeple Red Empire' on the tree 1989.
Figure 2:
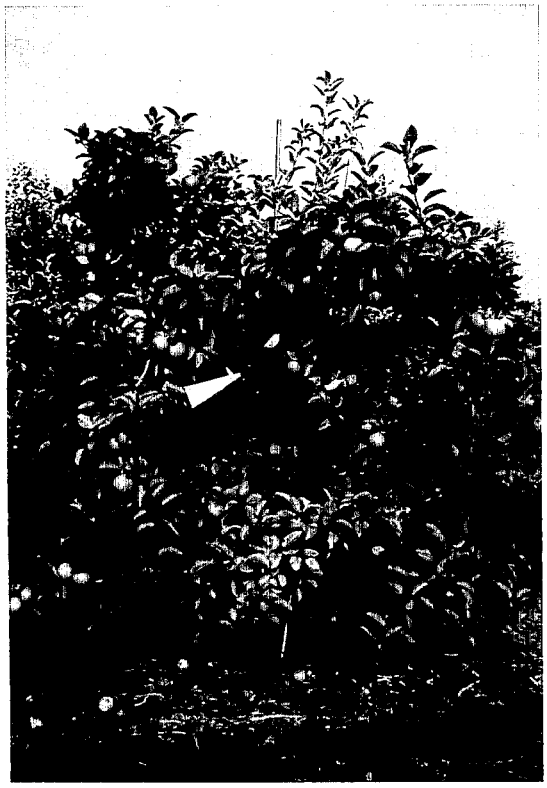
FIG. 2—Original tree on the 'Teeple Red Empire' was found. The sported part of the tree is above the arrow. Note the difference in color between the fruit from above the arrow and that from below the arrow.
Figure 3A:
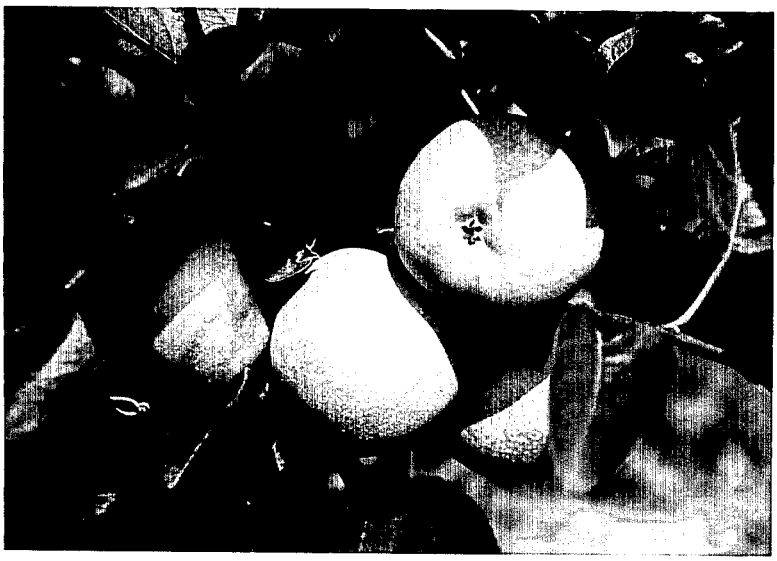
FIG. 3—Comparison of the color of the fruit of 'Empire' 3A and the 'Teeple Red Empire' 3B on the sported tree Aug. 31, 1989.
Figure 3B:
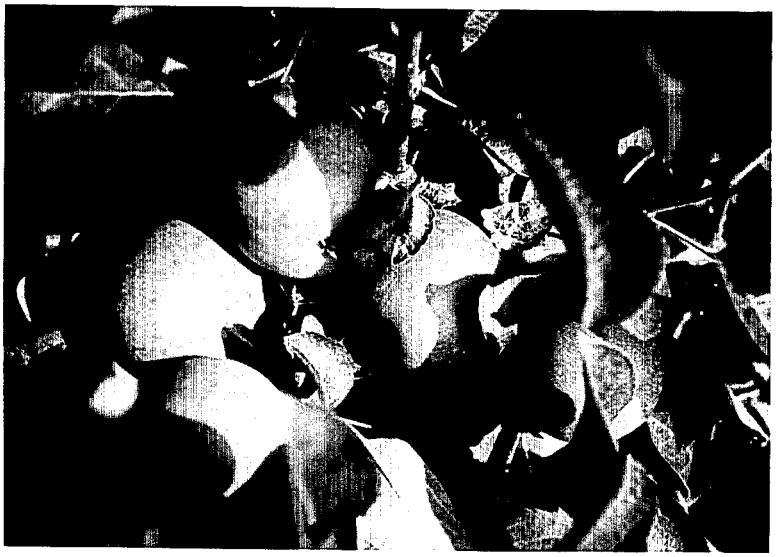
Figure 4:
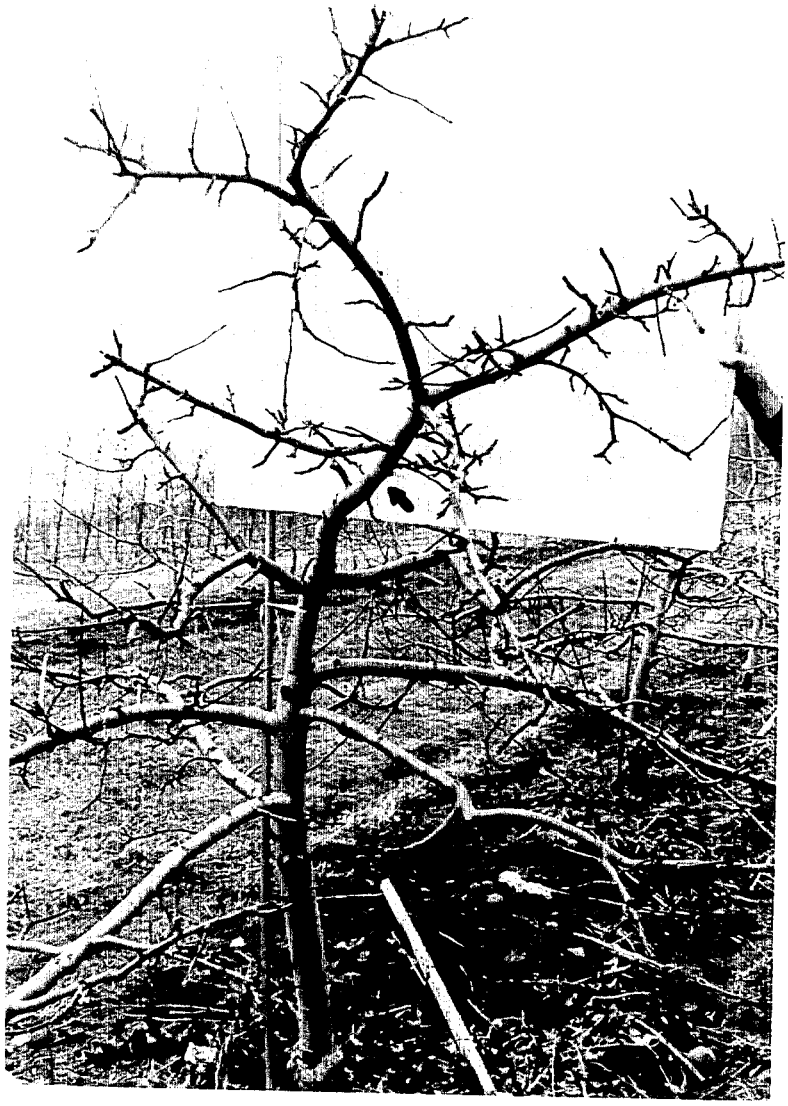
FIG. 4—The 'Empire' tree on which the red sport occurred. See the plastic tape of marking the extent of the sported part of the tree.
Figure 5A:
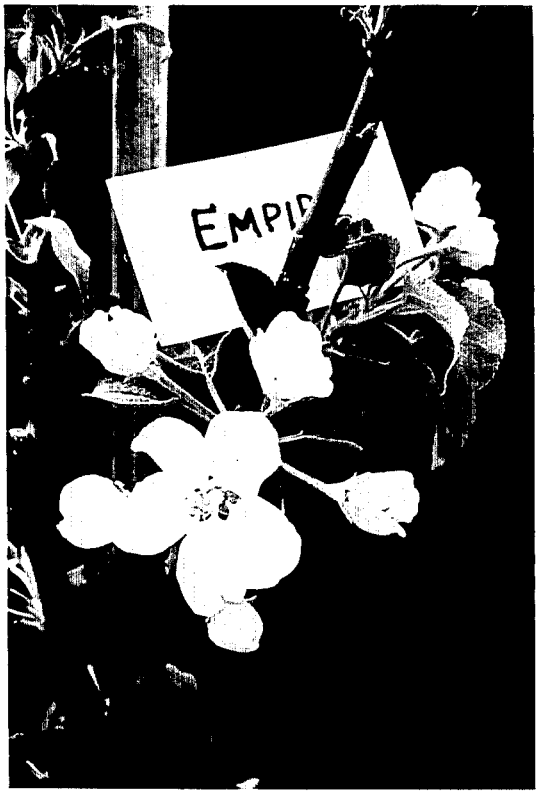
FIG. 5—Comparison of the blossoms on an 'Empire' 5A tree and a 'Teeple Red Empire' tree 5B, 5/24/89.
Figure 5B:
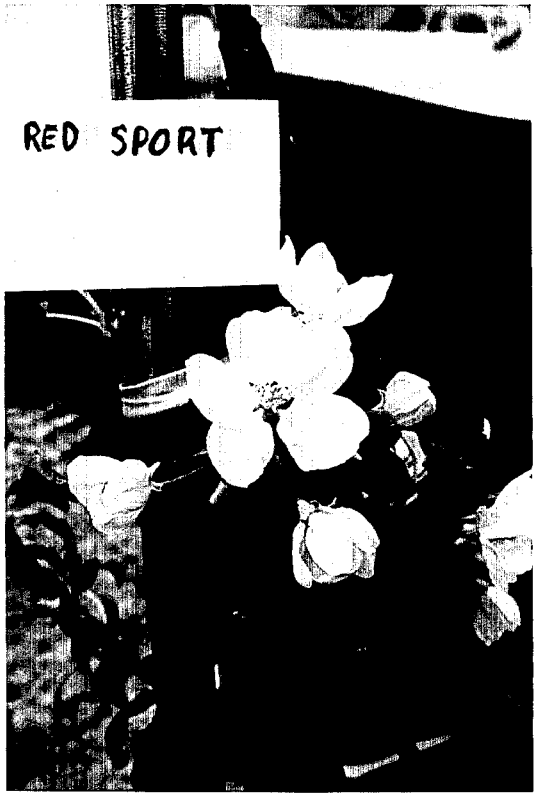
Figure 6A:
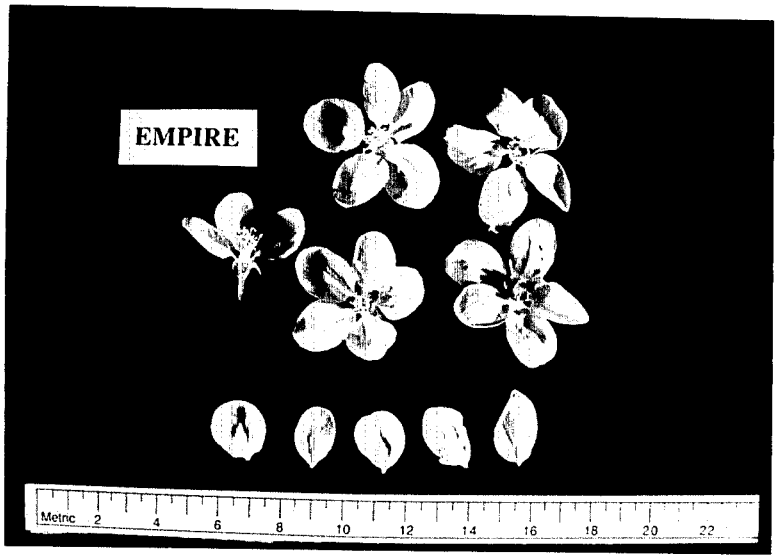
FIG. 6—Detailed comparison of the flowers of 'Empire' 6A and of the 'Teeple Red Empire' 6B.
Figure 6B:
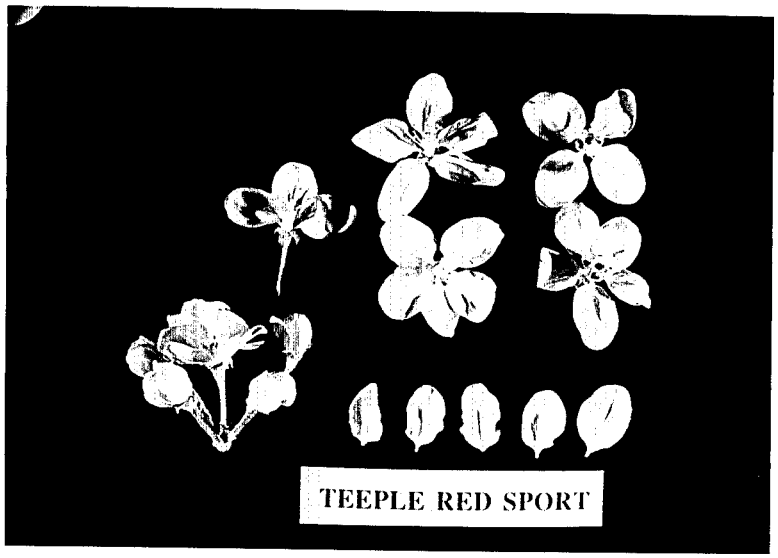
Figure 7:
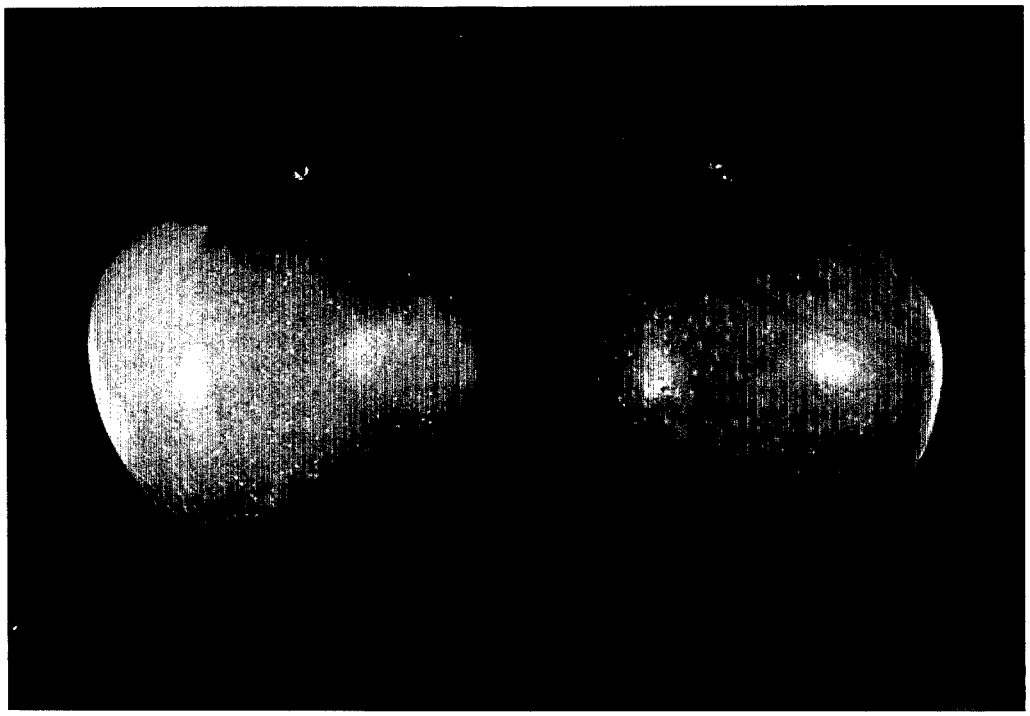
FIG. 7—Compares the fruit of 'Empire' and 'Teeple Red Empire' from the same orchard in 1990.

Color readings were taken on 'Teeple Red Empire' and standard 'Empire' from the 1990 crop. Using the "Dictionary of Color" (A. Maerz and M. R. Paul, 1950 McGraw Hill, N.Y.), the color of the standard 'Empire' is found on page 35, plate 6, section 6L and is dark cardinal. The color of 'Teeple Red Empire' is found on page 37, plate 7, section 7L an is maroon. This quantifies that the color and intensity of the red 'Teeple Red Empire' is deeper than the standard 'Empire'. These tests were made on fruit from the same aged trees of 'Teeple Red Empire' and standard 'Empire' growing in the same orchard, on the same rootstock. Fruit coloration differences were evident from four and one-half weeks prior to harvest. FIG. 7 shows a standard 'Empire' (left) compared to a 'Teeple Red Empire' (right) two and one-half weeks before harvest. These are two random samples from trees in the same orchard, on the same rootstock and of the same age.

In 1990 solid rows of 'Teeple Red Empire' adjacent to standard 'Empire' trees of the same age and on the same rootstock were compared. All trees of 'Teeple Red Empire' observed were uniform in having darker fruit and with more of the surface covered by red than standard 'Empire'. Fruit coloration two and one-half weeks prior to harvest, ranged from 95% to 100% colored for 'Teeple Red Empire' compared to 60% to 100% colored fruit for standard 'Empire'. At harvest, 95% to 100% of 'Teeple Red Empire' fruit were colored compared to 80% to 100% of standard 'Empire'. 1990 was an excellent year for color development of 'Empire', so the contract between the fruit in standard cultivar was not as dramatic as it would be in low light years.

In addition to greater overall color, the fruit coloration of 'Teeple Red Empire' is much darker than standard red 'Empire', as evidenced by the color described here by color standards, as well as Hunter Color value data (Table 2), which compares the sun side and the shade side of the fruit and clearly demonstrates that 'Teeple Red Empire' is redder and far less light dependent for color than is 'Empire'.

HUNTER COLOR METER VALUES (L, a, and b)

| | EMPIRE (STANDARD) | | | | | |
|---|---|---|---|---|---|---|
| | Sun side | 90° | 180° | 270° | Mean | 180°-Sun |
| L | 26.6 | 27.3 | 46.1 | 27.3 | 31.8 | 19.5 |
| a | 21.2 | 21 | 13.7 | 21.8 | 19.4 | |
| b | 3.6 | 5.1 | 16 | 4.8 | 7.4 | |
| L | 27.7 | 37.1 | 38.4 | 31.8 | 33.8 | 10.7 |
| a | 19.5 | 21 | 19.4 | 21.6 | 20.4 | |
| b | 3.7 | 10.9 | 11.4 | 6.5 | 8.1 | |
| L | 25.5 | 24.6 | 32.1 | 26.6 | 27.2 | 6.6 |
| a | 16.1 | 18.3 | 20.5 | 18.1 | 18.3 | |
| b | 2.5 | 2.6 | 8.4 | 3.6 | 4.3 | |
| L | 25 | 29.6 | 35.1 | 30.4 | 30.0 | 10.1 |
| a | 25.6 | 19.8 | 19.2 | 17.3 | 20.5 | |
| b | 2.4 | 6.1 | 10.5 | 5.4 | 6.1 | |
| L | 27.3 | 34.1 | 39.4 | 35.3 | 34.0 | 12.1 |
| a | 18.5 | 18.7 | 17 | 18 | 18.1 | |
| b | 4.1 | 9.2 | 13.1 | 10.3 | 9.2 | |
| | | | | | Grand mean | 11.8 |

| | TEEPLE EMPIRE | | | | | |
|---|---|---|---|---|---|---|
| | Sun side | 90° | 180° | 270° | Mean | 180°-Sun |
| L | 25.9 | 28.7 | 26.6 | 24.8 | 26.5 | 0.7 |
| a | 13.8 | 22.1 | 15.9 | 12.9 | 16.2 | |
| b | 1.4 | 6.4 | 2.9 | 1.5 | 3.1 | |
| L | 27.5 | 28.7 | 27.7 | 25.5 | 27.4 | 0.2 |
| a | 13.4 | 20.9 | 18 | 13.2 | 16.4 | |
| b | 1.9 | 5.2 | 3.4 | 1.2 | 2.9 | |
| L | 24 | 26.3 | 27.2 | 24.4 | 25.5 | 3.2 |
| a | 10.3 | 15.4 | 20.1 | 12.3 | 14.5 | |
| b | 0.1 | 1.2 | 3.9 | 0.3 | 1.4 | |
| L | 23.2 | 25.7 | 27.3 | 24.4 | 25.2 | 4.1 |
| a | 11 | 13.6 | 17.7 | 13.9 | 14.1 | |
| b | 0.4 | 1.1 | 3.5 | 0.3 | 1.3 | |
| L | 24.6 | 29.2 | 26.3 | 25.5 | 26.4 | 1.7 |
| a | 11.7 | 20 | 18.7 | 14.5 | 16.2 | |
| b | 1.6 | 5.5 | 4.1 | 1.5 | 3.2 | |

-continued

| HUNTER COLOR METER VALUES (L, a, and b) | |
|---|---|
| Grand mean | 1.98 |

For L values the higher the number the lighter the color. If you compare the sun side of the fruit, the values of the two are similar. However, 180 degrees from the sun side (or the side likely to be in the shade), there are higher values in the standard but not the sport. The change averages 11.80 for standard Empire, and 1.98 for the sport. This indicates the uniformity of pigmentation in the sport.

All values obtained using a Hunter color meter. Five fruits sampled randomly from trees of the same age and on the same rootstock.

Merits

The outstanding merit of 'Teeple Red Empire' is its excellent red color. Growers will be able to get high packouts of fancy grade fruit and the customer will choose the redder fruit over the less well colored fruit.

We claim:

1. A new and distinct apple cultivar as herein described and illustrated, which has fruit redder than 'Empire', but which in all other aspects is similar to 'Empire'.

* * * * *